United States Patent [19]
Gilbert et al.

[11] Patent Number: 6,042,822
[45] Date of Patent: *Mar. 28, 2000

[54] INTERFERON POLYMER CONJUGATES

[75] Inventors: Carl W. Gilbert, Powder Springs, Ga.; Myung-ok Park-Cho, Seoul, Rep. of Korea

[73] Assignee: Enzon, Inc., Piscataway, N.J.

[*] Notice: This patent is subject to a terminal disclaimer.

[21] Appl. No.: 09/287,476

[22] Filed: Apr. 6, 1999

Related U.S. Application Data

[63] Continuation of application No. 08/994,622, Dec. 19, 1997, Pat. No. 5,951,974, which is a continuation-in-part of application No. 08/337,567, Nov. 10, 1994, Pat. No. 5,711,944, which is a continuation-in-part of application No. 08/150,643, Nov. 10, 1993, abandoned.

[51] Int. Cl.[7] .......................... A61K 38/21; C07K 1/113; C07K 14/56

[52] U.S. Cl. ...................... 424/85.7; 530/351; 530/409; 530/410; 530/411

[58] Field of Search ................. 424/85.4, 85.7; 530/351, 409, 410, 411

[56] References Cited

U.S. PATENT DOCUMENTS

| | | | |
|---|---|---|---|
| 4,179,337 | 12/1979 | Davis et al. | 435/181 |
| 4,275,000 | 6/1981 | Ross | 435/188 |
| 4,609,546 | 9/1986 | Hiratani | 530/351 |
| 4,680,338 | 7/1987 | Sundoro | 525/54.1 |
| 4,766,106 | 8/1988 | Katre et al. | 514/12 |
| 4,810,638 | 3/1989 | Albarella et al. | 435/7 |
| 4,894,226 | 1/1990 | Aldwin et al. | 424/85.2 |
| 4,897,471 | 1/1990 | Stabinsky | 536/27 |
| 4,904,582 | 2/1990 | Tullis | 435/172.3 |
| 4,917,888 | 4/1990 | Katre et al. | 424/85.91 |
| 4,935,465 | 6/1990 | Garman | 525/54.1 |
| 5,004,605 | 4/1991 | Hershenson et al. | 530/351 |
| 5,109,120 | 4/1992 | Ueno et al. | 530/351 |
| 5,122,614 | 6/1992 | Zalipsky | 548/520 |
| 5,281,698 | 1/1994 | Niteeki | 530/351 |
| 5,283,317 | 2/1994 | Saifer et al. | 528/405 |

(List continued on next page.)

FOREIGN PATENT DOCUMENTS

| | | |
|---|---|---|
| 0154316 | 9/1985 | European Pat. Off. . |
| 0236987 | 9/1987 | European Pat. Off. . |
| 0510356 | 10/1992 | European Pat. Off. . |
| 0584876 | 3/1994 | European Pat. Off. . |
| 0 809 996 A2 | 12/1997 | European Pat. Off. ....... A61K 47/48 |
| 0 593 868 B1 | 4/1998 | European Pat. Off. ........ C07K 14/56 |
| WO9101758 | 2/1991 | WIPO . |
| WO9216555 | 10/1992 | WIPO . |
| WO96/11953 | 4/1996 | WIPO . |

OTHER PUBLICATIONS

Borukhov et al. Chemical Modification of the Recombinant . . . Biochem. Biophys. Res. Comm. vol. 167, No. 1, pp. 74–80, Feb. 28, 1990.

(List continued on next page.)

*Primary Examiner*—Jeffrey E. Russel
*Attorney, Agent, or Firm*—Roberts & Mercanti, LLP

[57] ABSTRACT

Compositions containing alpha interferon conjugated to a substantially non-antigenic polymer are disclosed in which at least about 30% of the conjugates include covalent attachment of the alpha interferon to the substantially non-antigenic polymer at a histidine. Also disclosed is a process for preparing the conjugates. The process includes contacting an alpha interferon with a succinimidyl carbonate-activated substantially non-antigenic polymer at a pH which is sufficient to facilitate covalent attachment of the polymer on a histidine of the alpha interferon.

22 Claims, 2 Drawing Sheets

U.S. PATENT DOCUMENTS

| | | | |
|---|---|---|---|
| 5,382,657 | 1/1995 | Karasiewicz et al. | 530/351 |
| 5,468,478 | 11/1995 | Saifer et al. | 424/78.27 |
| 5,539,063 | 7/1996 | Hakimi et al. | 525/403 |
| 5,559,213 | 9/1996 | Hakimi et al | 530/351 |
| 5,646,242 | 7/1997 | Baker et al. | 530/303 |
| 5,650,234 | 7/1997 | Dolence et al. | 428/447 |
| 5,676,942 | 10/1997 | Testa | 424/85.7 |
| 5,711,944 | 1/1998 | Gilbert et al. | 424/85.7 |
| 5,738,846 | 4/1998 | Greenwald et al. | 424/85.7 |
| 5,747,646 | 5/1998 | Hakimi et al. | 530/351 |
| 5,762,923 | 6/1998 | Gross et al. | 424/85.7 |
| 5,951,974 | 9/1999 | Gilbert et al. | 424/85.7 |
| 5,981,709 | 11/1999 | Greenwald et al. | 530/351 |
| 5,985,263 | 11/1999 | Lee et al. | 424/85.2 |

OTHER PUBLICATIONS

Zalipsky, et al., Attachment of Drugs to Polyethylene Glycols. Eur. Polym. J., vol. 19, No. 12, pp. 1177–1183 (1983).

Goeddel, D.V. et al., The Structure of Eight Distinct Coloned Human Leukocyte Interferon cDNAs, Nature vol. 290; pp. 20–26; Mar. 5, 1981.

Zalipsky S. et al., Evaluation of a New Reagent for Covalent Attachment of Polyethylene Glycol to Proteins, Biotechnology and Applied Biochemistry, vol. 15; pp. 100–114; 1992.

Kontsek, P., Human Type I Interferons: Structure and Function, Acta Virologica, vol. 38; pp. 345–360; 1994.

Kinstler, O.B. et al., Characterization and Stability of N–terminally PEGYlated rhG–CSF, Pharmaceutical Res., vol. 13, No. 7; pp. 996–1002; 1996.

Monkarsh, S.P. et al., Positional Isomers of Monopegylated Interferon alpha–2a: Isolation, Characterization, and Biological Activity, Analytical Biochemistry, vol. 247; pp. 434–440; 1997.

Viscomi, G.C., Structure–activity of Type I Interferons, Biotherapy, vol. 10; pp. 59–86; 1997.

Gotoh, Y., et al. Chemical Modification of Silk Fibroin with Cyanuric Chloride–Activated Poly(ethylene glycol): Analysis of Reaction by H–NMR Spectroscop and . . . , Bioconjugate Chem, vol. 4; pp. 554–559; 1993.

Lundblad, R.L., et al. Chemical Reagents for Protein Modification, CRC Press, Inc., vol. 1; pp. 105–125; 1988.

Shearwater Polymers, Inc. *Catalog,* p. 45; Jan. 1996.

INTERFERON POLYMER CONJUGATES

This application is a continuation os U.S. patent application Ser. No. 08/994,622, filed on Dec. 19, 1997, which has now issued as U.S. Pat. No. 5,951,974, which, in turn, is a continuation-in-part of U.S. patent application Ser. No. 08/337,567, filed Nov. 10, 1994, now U.S. Pat. No. 5,711,944 which, in turn, is a continuation-in-part of U.S. patent application Ser. No. 08/150,643, filed Nov. 10, 1993, now abandoned. The contents of each application are incorporated herein by reference.

BACKGROUND OF THE INVENTION

1. Field of the Invention

The present invention is directed to interferon-polymer conjugates. In particular, the invention is directed to conjugates having a novel interferon-polymer attachment profile.

2. Description of Related Art

Conjugating biologically-active proteins to polymers has been suggested to improve one or more of the properties of circulating life, water solubility or antigenicity in vivo. For example, some of the initial concepts of coupling peptides or polypeptides to polyethylene glycol (PEG) and similar water-soluble polymers are disclosed in U.S. Pat. No. 4,179,337, the disclosure of which is incorporated herein by reference.

Insulin and hemoglobin were among the first therapeutic agents conjugated. These relatively large polypeptides contain several free lysine ε-amino attachment sites. Several polymers could be attached without significant loss of biologic activity.

For many biologically active materials, the conjugation process, however, is not without complications. Care must be taken to limit the loss of biological activity caused by the conjugation reaction. For example, if too much of the activated polymer is attached to the target protein or polypeptide, biological activity can be severely reduced or lost. Further, if the wrong linker joining the polymer to the protein is used or an insufficient amount of polymer is attached to the target, the therapeutic value of the resultant conjugate is rather limited. Often, such conjugates do not demonstrate enough of an increase in the circulating life to compensate for the loss in bioactivity. Problems can also result when a therapeutic moiety's active site (i.e. where groups associated with bioactivity are found) becomes blocked as a result of the polymer attachment. This problem can be difficult to avoid since the polymer and protein are typically joined in solution-based reactions. Pre-blocking the active sites with materials such as pyridoxal phosphate has been suggested, but the results have been inconsistent. The problems are particularly acute with lower molecular weight proteins and peptides. These bioactive materials often have few attachment sites not associated with bioactivity.

Interferons, hereinafter also referred to as IFN's, are a particular example of proteins which could benefit from improved polymer conjugation techniques. See, for example, U.S. Pat. Nos. 4,766,106 and 4,917,888 which describe inter alia beta interferon conjugated with activated polymers including mPEG-2,4,6-trichloro-S-triazine, mPEG-N-succinimidyl glutarate or mPEG-N-succinimidyl succinate. The patentees disclose that covalent modification of the protein is done at a pH of from 5 to 9 and, when the protein is reacted through its lysine residues, covalent modification of the protein is done at a pH of from 8 to 9. Relatively high molar excesses (10, 20 and 50-fold) of the activated polymer are also used.

European Patent Application bearing publication No. 0 236 987 describes reacting alpha and gamma interferons with high molar excesses of alkyl imido ester-activated polyethylene glycols under conditions which preferably include a pH of from approximately 7 to 9. European Patent Application bearing publication No. 0 510 356 describes conjugating alpha interferon with pyridinyl carbonyl and thiocarbonyl activated PEG at a pH of from 7 to 9. There was no mention in these disclosures that amino acids other than lysine were involved in the conjugation or that it would be advantageous to do so.

In spite of the above-described disclosures, most interferon-polymer conjugates have been deemed to be unacceptable for one reason or another.

The present invention addresses these shortcomings.

SUMMARY OF THE INVENTION

In one aspect, the present invention includes pharmaceutical compositions containing a mixture of mono-polymer stranded alpha interferon conjugates. In the mixture, individual mono-polymer-IFN conjugates are defined as positional isomers, depending upon which amino acid residue is covalently attached to the polymer. Within this mixture is an isomer which is an alpha interferon covalently conjugated to a polymer at a histidine residue on the alpha interferon. The compositions are distinguishable from prior art products in part due to the fact that at least about 15%, and preferably at least about 30%, of the interferon conjugates included as part of the composition have a polymer covalently attached to a histidine of the alpha interferon. Preferably, however, the conjugates or positional isomers contain about one polymer strand per alpha interferon, regardless of where the polymer is attached.

Still further aspects of the invention include methods of preparing alpha-interferon conjugates and compositions prepared by the methods. The IFN-polymer conjugates are prepared by reacting a solution containing alpha interferon with a sufficient amount of an oxycarbonyl-N-dicarboximide-activated polymer such as a succinimidyl carbonate activated PEG under conditions which are sufficient to effect covalent attachment of the polymer to the interferon, at least in part, to a His residue such as the His34 of alpha interferon. Part of these conditions include conducting the conjugation reaction within a pH range which is sufficient to facilitate covalent attachment of at least a portion of the polymer strands to histidine residue amino groups of the interferon molecules.

Suitable alpha-interferons include recombinant and non-recombinant alpha-interferons isolated from mammals. The polymer portion of the conjugate is preferably a polyalkylene oxide (PAO), such as a monomethoxy polyethylene glycol (mPEG). In alternative embodiments, other substantially non-antigenic polymers can also be used. The polymers preferably have a molecular weight of from about 200 to about 35,000.

The conditions for effecting conjugation include conducting the attachment reaction with from about an equi-molar to about a relatively small molar excess of the activated polymer with respect to the alpha-interferon. The conditions further include conducting the reaction at a pH of less than about 7 and preferably at a pH of from about 4.5 to about 6.8.

The invention also includes methods of treating alpha-interferon susceptible conditions in mammals. In this aspect, the treatment includes administering an effective amount of the composition containing the IFN conjugates described herein to mammals requiring such therapy.

Thus, the present invention further provides for an alpha-interferon-conjugate, including an alpha-interferon having attached thereto an amount of a substantially non-antigenic polymer so that the conjugate has a $T_{max}$ at least about 4 times greater than unmodified alpha-interferon measured under the same conditions, or even a $T_{max}$ that is at least about 8 times greater than unmodified alpha-interferon measured under the same conditions.

In an additional feature, the present invention provides for an alpha-interferon-conjugate, including an alpha-interferon having attached thereto an amount of a substantially non-antigenic polymer such as so that the conjugate has an AUC at least about 10 times that of unmodified alpha-interferon measured under the same conditions.

In a further additional feature, the conjugate has at least about 10% of the activity of unmodified alpha-interferon measured under the same conditions when the conjugate is administered subcutaneously in a mammal, including when the conjugate has an AUC at least about 10 times that of unmodified alpha-interferon measured under the same conditions. Optionally, the conjugate also has a $T_{1/2}$, of about 5 hours alpha phase when said conjugate is administered subcutaneously in a mammal, including when the conjugate has an AUC at least about 10 times that of unmodified alpha-interferon measured under the same conditions.

Preferably, the substantially non-antigenic polymer employed to achieve conjugates with the above-described pharmacokinetic parameters is a polyalkylene oxide, and more preferably, the polyalkylene oxide is a polyethylene glycol.

More preferably, the invention provides for a composition that includes a mixture of alpha-interferon conjugate positional isomers, wherein one of the positional isomers includes an alpha interferon covalently conjugated to a substantially non-antigenic polymer, such as, for example, an alkyl terminated polyalkylene oxide, at a histidine residue on the alpha interferon, so as to provide the above-described pharmacokinetic properties.

As a result of the present invention, it has been unexpectedly found that additional improvements in interferon-polymer conjugate compositions are possible. For example, by modifying the conjugation conditions, it is now possible to obtain compositions containing relatively high activity mono-polymer IFN conjugates in which a portion of the alpha interferon is attached at unique locations to polymers. In addition, it has been found that conducting the conjugation reaction with succinimidyl carbonate and some related oxycarbonyl-N-dicarboximide-type activated polymers, such as SC-PEG, at pH levels which are more acidic than that typically used for conjugation, will cause the polymer to attach not only at the expected lysine sites on the IFN molecule, but also selectively on histidine sites such as the preferred His34 amino acid on alpha interferons.

For a better understanding of the present invention, reference is made to the following description and drawings.

DETAILED DESCRIPTION OF THE INVENTION

1. Interferons

Figure 1:
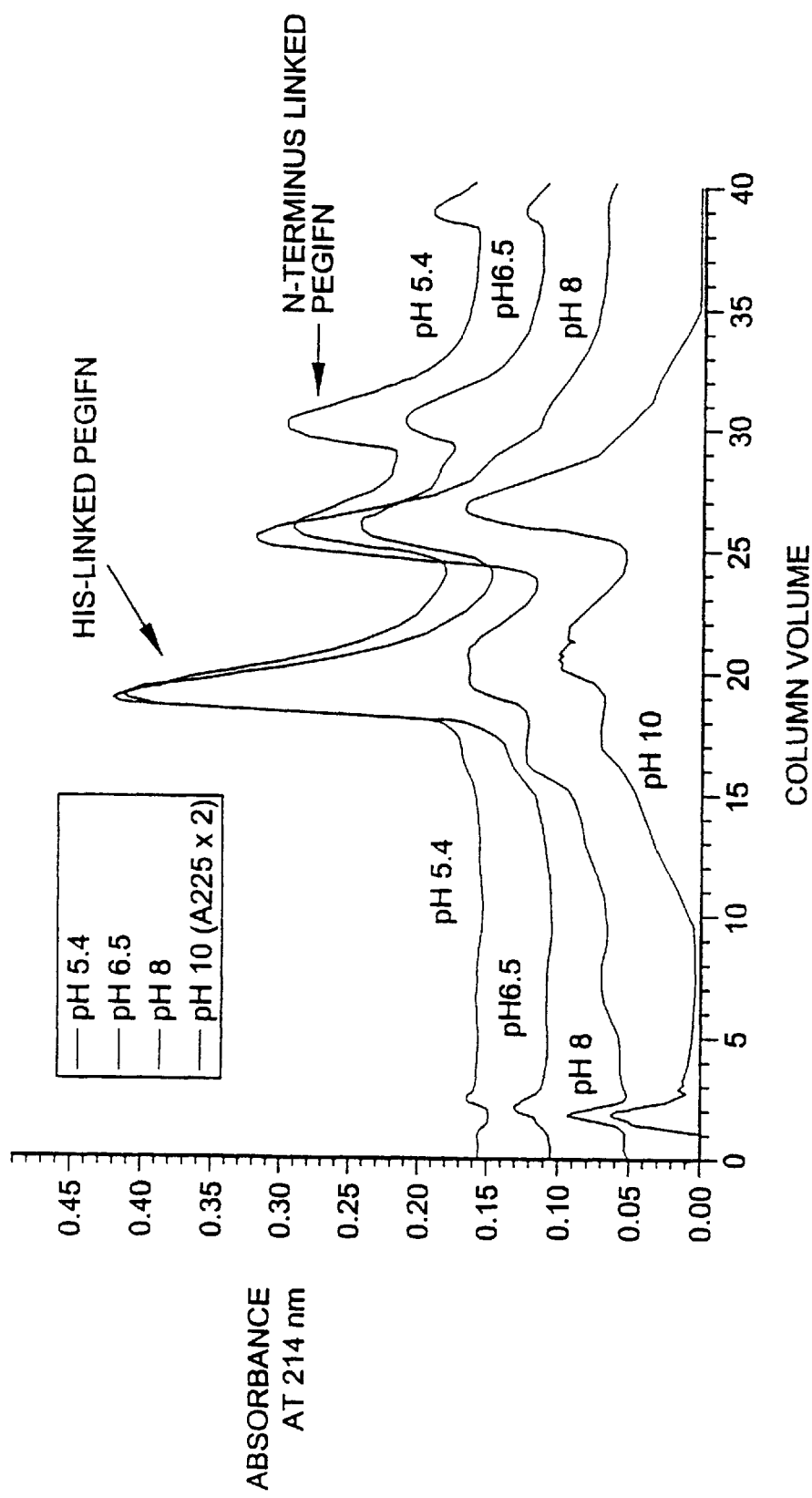
FIG. 1 is a series of chromatograms referred to in Example 11.

The interferon (IFN) portion of the polymer conjugate can be prepared or obtained from a variety of sources including recombinant techniques such as those using synthetic genes expressed in *E. coli*. See also Pestka, "Interferon α" in *Human Cytokines*, Black-well Scientific Publications 1–16 (1992), the disclosure of which is incorporated herein by reference. In addition, the IFN can also be a mammalian source extract such as human, ruminant or bovine αIFN. One particularly preferred IFN is IFNα-2b, a recombinantly-made product of the Schering Corp., Kenilworth, N.J.

The term "interferon" or "IFN" as used herein means the family of highly homologous species-specific proteins that inhibit viral replication and cellular proliferation and modulate immune response. Human interferons are grouped into three classes based on their cellular origin and antigenicity: α-interferon (leukocytes), β-interferon (fibroblasts) and γ-interferon (B cells). Recombinant forms of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. See also Viscomi, 1996 *Biotherapy* 10:59–86, the contents of which are incorporated herein by reference. The terms "α-interferon", "alpha interferon", "interferon alpha" and "human leukocyte interferon" are used interchangeably in this application to describe members of this group. Both naturally occurring and recombinant α-interferons, including consensus interferon such as that described in U.S. Pat. No. 4,897,471, the contents of which are incorporated herein by reference, may be used in the practice of the invention.

The purification of interferon alpha from human leukocytes isolated from the buffy coat fraction of whole blood is described in U.S. Pat. No. 4,503,035. Human leukocyte interferon prepared in this manner contains a mixture of human leukocyte interferons having different amino acid sequences. Purified natural human α-interferons and mixtures thereof which may be used in the practice of the invention include but are not limited to Sumiferon® interferon alpha-nI available from Sumitomo, Japan, Wellferon® interferon alpha-nI (Ins) available from Glaxo-Wellcome Ltd., London, Great Britain, and Alferon® interferon alpha-no available from the Purdue Frederick Co., Norwalk, Conn.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains its in vitro and in vivo antiviral and immunomodulatory activities. It is also understood that the recombinant techniques could also include a glycosylation site for addition of a carbohydrate moiety on the recombinantly-derived polypeptide.

The construction of recombinant DNA plasmids containing sequences encoding at least part of human leukocyte interferon and the expression in *E. coli* of a polypeptide having immunological or biological activity of human leukocyte interferon is disclosed in U.S. Pat. No. 4,530,901 and European Patent No. EP 0 032 134. The construction of hybrid a-interferon genes containing combinations of different subtype sequences (e.g., A and D, A and B, A and F) is disclosed in U.S. Pat. Nos. 4,414,150, 4,456,748 and 4,678,751. Typical suitable recombinant α-interferons which may be used in the practice of the invention include but are not limited to interferon alpha-2b such as Intron® A available from Schering Corporation, Kenilworth, N.J., interferon alpha-2a such as Roferon® A available from Hoffmann-La Roche, Nutley, N.J., and Infergen® available form Amgen, Thousand Oaks, Calif.

Alternate embodiments, where the foreign αIFN is not completely autologous, may be also used if desired. A key, however, is that the non-autologous αIFN has sufficient bioactivity or αIFN effect such as antiviral activity in the target mammal. Other substances including αIFN fractions or predecessor polypeptides can also be included in the conjugates of the present invention. As used herein, "α-IFN effect in mammals" means in vivo activity corresponding to that observed with αIFN's. These substances are prepared by using techniques known to those of ordinary skill in the art such as tissue culture, extraction from animal sources or by recombinant DNA methodologies. Transgenic sources of αIFN and related moieties are also contemplated. Such materials are obtained from transgenic animals, i.e. mice, pigs, cows, etc. where the αIFN protein is expressed in milk, blood, or other tissues. The method by which the αIFN is prepared for the conjugates of the present invention is not limited to those described herein. For purposes of the present invention, the αIFN's are preferred because of their biochemical and serological properties. In particular, αIFN has documented antiviral properties and diffuses more effectively into the bloodstream than other interferons.

2. Non-Antigenic Polymers

To conjugate the IFN to polymers such as poly(alkylene oxides), one of the polymer hydroxyl end-groups is converted into a reactive functional group which allows conjugation. This process is frequently referred to as "activation" and the product is called an "activated" polymer or activated poly(alkylene oxide). Other substantially non-antigenic polymers are similarly "activated" or functionalized.

The activated polymers are reacted with αIFN so that attachment occurs at ε-amino groups of lysines, the N-terminal cysteine amino group and, as described below, at amino groups on histidines. Free carboxylic acid groups, suitably activated carbonyl groups, oxidized carbohydrate moieties and mercapto groups if available on the IFN can also be used as supplemental attachment sites, if desired.

In a preferred aspect of the invention, urethane (carbamate) linkages are formed between one of the αIFN amino acid amino groups (i.e. lysine, histidine, N-terminal), and the activated polymer. Preferably, the urethane linkage is formed using a terminal oxycarbonyl-oxy-N-dicarboximide group such as a succinimidyl carbonate group. Alternative activating groups include N-succinimide, N-phthalimide, N-glutarimide, N-tetrahydrophthalimide and N-norborene-2,3-dicarboxide. These urethane-forming groups are described in commonly owned U.S. Pat. No. 5,122,614, the disclosure of which is hereby incorporated by reference. This patent also discloses the formation of N-succinimide carbonate derivatives of polyalkylene oxides including polyethylene glycols which are also capable of forming urethane linkages with lysine amino group targets.

Among the substantially non-antigenic polymers, monoactivated, alkoxy-terminated polyalkylene oxides (PAO's), such as monomethoxy-terminated polyethylene glycols (mPEG's) are preferred; bis-activated polyethylene oxides (glycols) are also contemplated for purposes of cross-linking αIFN's or providing a means for attaching other moieties such as targeting agents for localizing the polymer-αIFN conjugate in a particular area such as, for example, the liver.

Suitable polymers will vary substantially by weight. Polymers having molecular number average weights ranging from about 200 to about 35,000 are usually selected for the purposes of the present invention. Molecular weights of from about 1,000 to about 15,000 are preferred and 2,000 to about 12,500 are particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof provided that the water solubility of the block copolymers is maintained. In addition to mPEG, $C_{1-4}$ alkyl-terminated polymers are also useful.

As an alternative to PAO-based polymers, effectively non-antigenic materials such as dextran, polyvinyl pyrrolidones, polyacrylamides such as HPMA's-hydroxypropylmethacrylamides, polyvinyl alcohols, carbohydrate-based polymers, copolymers of the foregoing, and the like can be used. Those of ordinary skill in the art will realize that the foregoing list is merely illustrative and that all polymer materials having the qualities described herein are contemplated. For purposes of the present invention, "substantially or effectively non-antigenic" means all materials understood in the art as being nontoxic and not eliciting an appreciable immunogenic response in mammals.

3. Reaction Conditions

Conjugation reactions, sometimes referred to as PEGylation reactions, are often carried out in solution without regard to where the polymer will attach to the protein. Such techniques are also usually carried out at slightly alkaline i.e. pH 7+ to about 9 for conjugating αIFNs. A key to the present invention, however, is that the retained IFN bioactivity can be maximized if the polymer is attached to a histidine, preferably His34 on IFNα 2b. It will be appreciated by the artisan that although various species of the αIFN may or may not have a histidine at amino acid 34, the interferon conjugates will nonetheless preferably include at least some positional isomers containing a polymer attached at an available histidine.

The processes of the present invention therefore includes reacting a solution containing an alpha interferon with an amount of an oxycarbonyl-oxy-N-dicarboximide-activated polymer such as succinimidyl carbonate-activated MPEG at a pH which is sufficient to facilitate covalent attachment of at least a portion of the polymer strands to a histidine, such as the His34 of IFNα2b, of the individual interferon molecules. In particular, the pH will preferably be slightly acidic, i.e. less than about 7.0; more preferably, less than about 6.8 and most preferably in the range of from about 4.5 to about 6.8.

The reaction conditions for effecting conjugation further include conducting the attachment reaction with from about equi-molar to about a relatively small molar excess of the activated polymer with respect to the alpha-interferon. In this regard, the process can be carried out with about 1–8-fold molar excesses; preferably about 1.5–7-fold molar excesses and most preferably about 1.75–5-fold molar excesses. The conjugation reaction can be carried out at about room temperature, 20–25° C. It is also preferred that the coupling reaction be allowed to proceed for rather short periods of time, i.e. 1–2 hours, before quenching. In practice, the reaction conditions provide a mixture of polymer-IFN positional isomers. Preferably, each isomer contains a single polymer strand attached to the interferon via an amino acid residue. In alternative embodiments, there can be more than one strand of polymer attached as a result of the process. Solutions containing these conjugates are also useful as is or can be further processed to separate the conjugates on the basis of molecular weight.

Characterization of the preferred one polymer strand-IFN conjugates (isomers) via cation exchange chromatography into separated peaks revealed that the polymer can be attached at up to about eight different sites on the IFNα2b molecule. These sites, representing individual positional isomers, are Cys1, Lys31, His34, Lys49, Lys83, Lys121, Lys131, Lys134. In some preferred embodiments, the reaction pools containing mono-polymer-IFN conjugates can contain relatively high proportions of the His34 positional isomer, i.e. about 30–60%, the Cys1 positional isomer, about 7–20%, and the Lys121 positional isomer, about 7–15%, with the rest of the positional isomers comprising the remainder. It will be understood that alternative IFN's will provide alternative distributions of positional isomers, depending upon the amino acid sequence of the starting material.

Due to the nature of the solution-based conjugation reactions, the compositions are a heterogeneous mixture of species which contain the polymer strand(s) attached at different sites on the interferon molecule. In any solution containing the conjugates, it is likely that a mixture of at least about 3, preferably about 6 and more preferably about 8 positional isomers will be present. For example, when IFNα2b is used, the solution will contain conjugate isomers with the polymer attached at one or more of Cys1, Lys31, His34, Lys49, Lys83, Lys121, Lys131, and Lys134 of the interferon. In the case of IFNα2b and the preferred forms of activated polymers described herein, the 3 most prominent sites of attachment are His34 (55%), Cys1 (15%) and Lys121 (15%).

A preferred composition of the invention is a mixture of the IFN-polymer isomers which are composed of at least about 15% His-polymer substituted-IFN. That is, at least about 15% of the conjugates include covalent attachment of the alpha interferon to the substantially non-antigenic polymer at a His. In more preferred aspects, at least about 30%, and in most preferred aspects of the invention, at least about 40% of the conjugates include the His34 covalent polymer attachment. When IFNα2b or related IFN's are used, the histidine attachment site is preferably His34.

4 Effect of Reaction pH Upon PEG-IFN Positional Isomers Distribution

The process of the present invention takes advantage of the discovery that the site of polymer attachment on alpha interferon is influenced to a large extent by the pH of the reaction system. As the pH of the reaction solution is varied, the reactivity towards specific forms of activated polymers of the various functional groups such as alpha-amines, imidazoles and epsilon amines will vary. Typically, polymer conjugation reactions are carried out at basic pHs in order to maximize attachment at lysine epsilon amino groups. For example, Zalipsky et al. *Biotech & App. Biochem* Vol 15, p. 100–114; (1992) evaluated the SC-PEG reagent for PEGylation and reported that the optimal reactivity was at about pH 9.3. The method of the present invention, however, includes conducting the reaction at lower pH's in order to allow a portion of the activated polymer strands to attach to histidine amino groups and de-emphasize, but not eliminate, lysine sites for attachment.

Furthermore, it has also been found that the biological activity of the various polymer conjugate positional isomers unexpectedly differs, even when each of the positional isomers has the same degree of polymer substitution.

The method described herein affords novel attachment of polymers such as PEG to a specific histidine residue in IFN molecules. In preferred embodiments, the conjugation reaction results in a substantial amount, i.e. at least about 30% of the conjugates being linked at IFN histidine sites such as the His34 on IFNα2b.

It has also been unexpectedly determined that the relative distribution of the positional isomers is largely dependent upon the pH at which the conjugation reaction is carried out. Shifting the pH from basic to slightly acidic pH (5.5–6.5) favors the formation of conjugates linked at His34 on IFNα2b, and to a lesser extent, the N-terminus (Cys1). Using pH(8–10) during the conjugation reaction, on the other hand, favors the formation of lysine-related attachment sites, confirmed via cation exchange chromatography. In those situations where IFNα2b is not included, the His34 site, of course, may not always be present. The reaction conditions nonetheless allow covalent attachment of an activated polymer to a His. Thus, Applicants have demonstrated that the pH of the reaction system influences the placement of some types of activated polymers on a protein surface, especially with regard to different amino acid residues (i.e. lysine vs. N-terminal amine vs. histidine).

5. Fractionation of Conjugates

Although the inventive process produces a substantial amount of conjugates having a single polymer strand, conjugates having varying degrees of polyalkylene oxide substitution are also generated. Residual unconjugated PAO's and αIFN can also be present. This mixture is typically in a reaction buffer containing one or more of phosphate, chloride and bicarbonate anions. The PAO, αIFN and conjugate mixture is preferably fractionated in a buffer solution containing from about 1–10 mg/ml PAO-αIFN conjugates. Suitable fractionating solutions have a pH of from about 7.0 to about 9.0 and preferably from about 7.5 to about 8.5. The solutions preferably contain one or more buffer salts selected from KCl, NaCl, $K_2HPO_4$, $KH_2PO_4$, $Na_2HPO_4$, $NaH_2PO_4$, $NaHCO_3$, $NABO_4$, $(NH_4)_2CO_3$ and glycine NaOH. Sodium phosphate buffers are preferred.

Depending upon the reaction buffer, the αIFN-polymer conjugate containing solution may first have to undergo buffer exchange/ultrafiltration. For example, the αIFN conjugate solutions can be ultra filtered across a low molecular weight cut-off (10,000 to 30,000 Dalton) membrane which will also remove most surfactants, if present, as well.

The fractionation of the conjugates into desired species is preferably carried out using an anion exchange medium. Such media are capable of selectively binding those αIFN-polymer conjugates having 1–4 polymer strands, excess polymer and unmodified αIFN. This fractionation occurs since the αIFN molecules of various degrees of substitution will have isoelectric points which vary in a somewhat predictable fashion. For example, the isoelectric point of αIFN is determined by the number of available amino groups available on the surface of the protein. These amino groups also serve as the point of attachment of polyalkylene oxide conjugates. Therefore, as the degree of substitution of polyalkylene oxide increases, the isoelectric point decreases, and the ability of the conjugate to bind to an anion exchange resin weakens.

The use of strongly polar anion exchange resins is especially preferred for the method of the present invention. For this reason, quaternary amine coated anion exchange resins are utilized. The quaternary amine resin may be coated onto either a polymeric or silica matrix; however, polymeric matrices are preferred. A number of tetramethylamine, or quaternary methylamine, anion exchange resins are commercially available, coated onto the support matrices. Included among the commercially available quaternary anion exchange resins suitable for use with the present invention are Q-HD available from Bio-Sepra; QA TRISACRYL® and QMA-SPHEROSIL®, quaternary amine resins coated onto a polymer matrix, manufactured by IBF of Garenne, France, for Sepracor, Inc. of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Millford, Mass. and PEI resins manufactured by JT Baker of Phillipsburg, N.J., may also be used.

The anion exchange resin is packed in the column and equilibrated by conventional means. A buffer having the same pH and osmolality as the conjugated αIFN solution is used. The conjugate-containing solution is then adsorbed onto the column. At the completion of the loading, a gradient flow of an elution buffer with increasing salt concentrations is applied to the column to elute the desired fractions of polyalkylene oxide-conjugated αIFN. The fractions are of essentially uniform molecular weight and degree of substitution.

Preferred IFN conjugate fractions have 14 polymer strands per αIFN molecule. More preferably, the fraction contains about 1–2 and, most preferably, about 1 polymer strand per αIFN molecule. The elution buffer preferably contains one or more salts selected from KCl, NaCl, $K_2HPO_4$, $KH_2PO_4$, $NAHPO_4$, $NaH_2PO_4$, $NaHCO_3$, $NaBO_4$ and $(NH_4)_2CO_3$. These fractions are substantially free of other conjugates. Any unconjugated species can then be backwashed from the column by conventional techniques.

Techniques utilizing multiple isocratic steps of increasing concentration can also be used. Multiple isocratic elution steps of increasing concentration will result in the sequential elution of αIFN-polymer conjugates. The degree of polymer conjugation within each fraction will be substantially uniform. However, the degree of polymer conjugation for each fraction will decrease with elution time. Ion exchange purification of the conjugates can also be carried out with, for example, a Q-HD Column from Sepracor, Inc. along with a dilute sodium phosphate solution (10 mM $NAPO_4$ ion). The sample is washed with 10 mM $NaPO_4$ to remove any unreacted PAO and thereafter a step gradient elution with NaCl is used. Elution with 10 mM NaCl recovers fractions containing conjugates with greater than 3 polymer strands PAO per IFN; elution with 50 mM NaCl recovers conjugates containing 1–2 strands; elution with 150 mM NaCl recovers unmodified EFN.

The temperature range for elution is between about 4° C. and about 25° C. Preferably, elution is carried out at a temperature of from about 6° C. to about 22° C. The elution of the PAO-αIFN fraction is detected by UV absorbance at 254 nm. Fraction collection may be achieved through simple time elution profiles. The preferred fractions can also be pooled in the elution buffer.

6. Surfactants

In another preferred aspect, the reaction conditions include the presence of a surfactant. The surfactants used in the processes of the present invention are ionic-type agents. One particularly preferred agent is sodium dodecyl sulfate, (SDS). Other ionic surfactants such as lithium dodecyl sulfate, quaternary ammonium compounds, taurocholic acid, caprylic acid, decane sulfonic acid, etc. can also be used. Non-ionic surfactants can also be used. For example, materials such as polyoxyethylene sorbitans (TWEEN®s), polyoxyethylene ethers (Tritons) can be used. See also Neugebauer, *A Guide to the Properties and Uses of Detergents in Biology and Biochemistry* (1992) Calbiochem Corp. The only limitations on the type of surfactant used in the processes of the invention are that they do not cause substantial denaturation of the IFN and do not completely inhibit polymer conjugation. The surfactants are present in the reaction mixtures in amounts from about 0.01–0.5%; preferably from 0.05–0.5%; and most preferably from about 0.075–0.25%. Mixtures of the surfactants are also contemplated.

7. Pharmacokinetic Parameters

As pointed out above, compositions of the present invention contain a heterogeneous mixture of polymer-IFN species in which the polymer strand(s) is/are attached at different sites on the interferon molecule. In spite of the heterogeneous nature of the conjugates, the compositions have a predictable in vivo pharmacokinetic profile which maximizes the therapeutic effect of the interferon.

Compositions of the present invention containing IFNα preferably include at least about 15% polymer-His conjugates, more preferably at least about 30% and most preferably at least about 40% polymer-His conjugates. While Applicants are not bound by theory, it is believed that the linkage for the His-positional isomers included in the compositions of the invention is relatively labile vis a vis that of the Lys-positional isomers. As a result, at physiologic pH, the compositions demonstrate a relatively smooth onset on activity after administration as well as a prolonged duration of effect. This profile allows the artisan to administer the composition in less frequent doses than with unmodified IFN's.

8. Methods of Treatment

Another aspect of the present invention provides methods of treatment for various medical conditions in mammals, preferably humans. The methods include administering an effective amount of an αIFN-polymer conjugate containing composition which has been prepared as described herein to a mammal in need of such treatment. The conjugates are useful for, among other things, treating interferon-susceptible conditions or conditions which would respond positively or favorably as these terms are known in the medical arts to interferon-based therapy.

Conditions that can be treated in accordance with the present invention are generally those that are susceptible to treatment with interferon alpha. For example, susceptible conditions include conditions which would respond positively or favorably as these terms are known in the medical arts to interferon alpha-based therapy. For purposes of the invention, conditions that can be treated with interferon alpha therapy include those conditions in which treatment with an interferon alpha shows some efficacy, but which may not be treatable with interferon alpha because the negative side effects outweigh the benefits of the treatment. For example, side effects accompanying alpha therapy have virtually ruled out treatment of Epstein Barr virus using interferon alpha. Practice of the invention results in substantially reduced or eliminated side effects as compared to conventional interferon alpha treatment.

Exemplary conditions which can be treated with interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6)), papilloma, poxvirus, picornavirus, adenovirus, rhinovirus, human T lymphotropic virus-type 1 and 2 (HTLV-1/-2), human rotavirus, rabies, retroviruses including human immunodeficiency virus (HIV), encephalitis and respiratory viral infections. The method of the invention can also be used to modify various immune responses.

Variants of interferon alpha are currently approved in the United States and other countries for the treatment of hairy cell leukemia, venereal warts, Kaposi's Sarcoma, and chronic non-A/non-B hepatitis: interferon alpha-2b, marketed under the trade name INTRON® A (Schering Corporation, Kenilworth N.J.), and interferon alpha-2a, marketed under the trade name Roferon® A (Hoffmann-La Roche, Nutley, N.J.), and consensus interferon marketed under the trade name Infergen™ (Amgen, Thousand Oaks, Calif.). Since interferon alpha-2b, among all interferons, has the broadest approval throughout the world for treating chronic hepatitis C infection, it is most preferred for use in the treatment of chronic hepatitis C in accordance with practice of the invention.

Administration of the described dosages may be every other day, but is preferably once or twice a week. Doses are usually administered over at least a 24 week period by injection.

Administration of the dose can be intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g. the severity of the neutropenia), the severity of the specific disease condition and the tolerance of the patient to the treatment as evidenced by local toxicity and by systemic side-effects. Dosage amount and frequency may be determined during initial screenings of neutrophil count.

Conventional pharmaceutical formulations can be also prepared using the conjugate-containing compositions of the present invention. The formulations comprise a therapeutically effective amount of the interferon-polymer conjugate composition together with pharmaceutically acceptable carriers. For example, adjuvants, diluents, preservatives and/or solubilizers, if needed, may be used in the practice of the invention. Pharmaceutical compositions of interferon including those of the present invention may include diluents of various buffers (e.g., Tris-HCl, acetate, phosphate) having a range of pH and ionic strength, carriers (e.g., human serum albumin), solubilizers (e.g., Polyoxyethylene Sorbitin or TWEEN®, polysorbate), and preservatives (e.g., thimerosol, benzyl alcohol). See, for example, U.S. Pat. No. 4,496,537.

The amount of the α-IFN polymer conjugate administered to treat the conditions described above is based on the IFN activity of the polymeric conjugate. It is an amount that is sufficient to significantly affect a positive clinical response. Although the clinical dose will cause some level of side effects in some patients, the maximal dose for mammals including humans is the highest dose that does not cause unmanageable clinically-important side effects. For purposes of the present invention, such clinically important side effects are those which would require cessation of therapy due to severe flu-like symptoms, central nervous system depression, severe gastrointestinal disorders, alopecia, severe pruritus or rash. Substantial white and/or red blood cell and/or liver enzyme abnormalities or anemia-like conditions are also dose limiting.

Naturally, the dosages of the various αIFN compositions will vary somewhat depending upon the αIFN moiety and polymer selected. In general, however, the conjugate is administered in amounts ranging from about 100,000 to about several million $IU/m^2$ per day, based on the mammal's condition. The range set forth above is illustrative and those skilled in the art will determine the optimal dosing of the conjugate selected based on clinical experience and the treatment indication.

The pharmaceutical compositions may be in the form of a solution, suspension, tablet, capsule, lyophilized powder or the like, prepared according to methods well known in the art. It is also contemplated that administration of such compositions will be chiefly by the parenteral route although oral or inhalation routes may also be used depending upon the needs of the artisan.

EXAMPLES

The following examples serve to provide further appreciation of the invention but are not meant in any way to restrict the effective scope of the invention.

Example 1

Preparation of rαIFN-PEG$_{5,000}$ in Presence of SDS (0.1%)

In this example, recombinant αIFN-2b, (rαIFN), a product of the Schering-Plough Corporation, Kenilworth, N.J. was conjugated with activated polyethylene glycol-N-succinimide carbonate (SC-PEG) as described in U.S. Pat. No. 5,122,614. The polymer had a molecular weight of about 5,000.

36 mg of the rαIFN was dialyzed into 0.1 molar sodium phosphate pH 7.5 using a Centricon-10 (a product of the Amicon Corporation of Beverly, Mass.). The final concentration of rαIFN was about 3 mg/ml. 0.1 ml of 10% SDS was added to the rαIFN and was allowed to incubate at room temperature for 10 minutes. Thereafter, 42 mg of SC-PEG$_{5,000}$ was added to the protein-SDS solution and stirred at room temperature for two hours and then quenched with glycine. Next, the reaction mixture was dialyzed into 10 mM sodium phosphate pH 8 to fractionate the PEGylated IFN using a Centricon-30.

Example 2

Preparation of rαIFN-PEG$_{12,000}$ in presence of SDS (0.1%)

In this Example, the steps of Example 1 were repeated except that the polyethylene glycol had a molecular weight of about 12,000. Reaction steps were exactly the same to provide the PEG$_{12,000}$ conjugate.

Example 3

Fractionation of 2PEG$_{5,000}$rαIFN

In this Example the conjugates prepared in accordance with Example 1 were fractionated to obtain the desired 2-PEG$_{5,000}$ fraction. The PEG-αIFN in sodium phosphate buffer was loaded onto a QHD anion exchange column. The 2-PEG fraction was eluted with a gradient from 0 to 400 mM sodium chloride in 10 mM phosphate pH 8. The 2-PEG fraction was verified using size exclusion chromatography and SDS-PAGE.

Example 4

Fractionation of 2PEG$_{12,000}$rαIFN

The polymer conjugates of Example 2 were fractionated in the manner described in Example 3 and verified in the same manner.

Examples 5–8

In these examples, additional preparations of $PEG_{12,000}$-rαIFN were prepared as described previously except that no surfactant was used. Following the conjugation reactions, the samples were tested for retained activity and PEG number. The results are provided below in the table.

TABLE 1

| IFN-$PEG_{12,000}$ PREPARATION | ACTIVITY (CPE) % OF CONTROL | PEG # |
| --- | --- | --- |
| Example 6 | 26 | 1.2 |
| Example 7 | 26 | 1.3 |
| Example 8 | 24 | 1.0 |

Example 9

Comparative Data

In this example, the product of Example 3, (SDS-2-$PEG_{5,000}$rαIFN), 2-$PEG_{5,000}$rαIFN made in the absence of a surfactant and unconjugated rαIFN were tested. Activity was determined using a CPE assay with EMC virus challenging A549 human lung carcinoma cells. Circulating life was determined using an average value obtained from the blood of 3 rats in a group receiving 1 million units, with time points taken over 7 days.

TABLE 2

|  | ACTIVITY (%) | VIRAL PROTECTION ASSAY $IC_{50}$ (pg/ml) | CIRCULATING HALF LIFE α PHASE (HRS.) |
| --- | --- | --- | --- |
| A. IFN-SDS 2-$PEG_{5,000}$ | 69 | 2.2 | 5.8 |
| B. IFN-$PEG_{5,000}$ | 30 | 4.0 | 6.8 |
| C. IFN | 100 | 1.5 | 0.17 |

This data clearly shows the advantages of the inventive process. Retained activity is over twice as great as that obtained using standard techniques.

Example 10

In this example, various pharmacokinetic data was generated using 2PEG-rαIFN conjugates prepared according to the methods described above. These samples were compared to unmodified IFN according to the protocol set out in Table 4. Sample B was prepared with SDS.

TABLE 3

| SAMPLE | PEG MOLECULAR WEIGHT | Retained Activity CPE ACTIVITY (% CONTROL) |
| --- | --- | --- |
| A | 5,000 | 35 |
| B | 5,000 | 69 |
| C | 12,000 | 26 |
| D | 12,000 | 26 |

TABLE 4

Pharmacokinetic Protocol

| | |
| --- | --- |
| ANIMALS: | Sprague Dawley (3 rates/time point) |
| DOSE: | $10 \times 10^6$ UN IFN/rat |
| ROUTE: | Subcutaneous (S.C.) |
| DRUG: | 2-PEG-IFNα's 5,000 and 12,000 mol. wt. PEG |
| TIME POINTS: | 0 min., 5 min., 15 min., 30 min., 1 hr., 2 hr., 4 hr., 8 hr., 24 hr., 48 hr., 5 days, and 7 days following drug administration. |
| ASSAY: | CPE Assay using serum samples in an EMC virus and A549 human lung carcinoma. |

Tables 5 and 6

Summary of Pharmacokinetics Data for PEG-Interferons

TABLE 5

| SAMPLE | $IC_{50}$ (pg/ml) | % ACTIVITY | AUC | Cmax (IU/ml) |
| --- | --- | --- | --- | --- |
| NATIVE IFNα | 1.52 pg/ml (N = 6) | 100% | 145,720 | 60,000 |
| A | 4.0 pg/ml (N = 3) | 35% | 348,920 | 24,433 |
| B | 2.2 ± 0.5 pg/ml (N = 3) | 69% | 351,037 | — |
| C | 5.8 ± 2.2 pg/ml (N = 3) | 26% | 1,574,682 | 62,750 |

TABLE 6

| SAMPLE | $T_{max}$ (hr) | T½α PHASE (hr) | T½β PHASE (HR) |
| --- | --- | --- | --- |
| NATIVE IFNα | 1 | 0.17 | — |
| A | 4 | 6.8 | 48 |
| B | 2–3 | 5.8 | — |
| C | 8 | 12.1 | 33 |

The foregoing data provide the following conclusions:

2-PEG-rαIFN conjugates prepared with both 5,000 and 12,000 molecular weight have distinct advantages over unmodified interferon in mammals. In the case of subcutaneously administered compositions, $T_{max}$ is substantially increased by the conjugation of the protein with about 2 PEG's. For chronic conditions, longer $T_{max}$'s are desirable and allow clinicians to space out recurring administrations due to the lengthening of the duration of effect. Even more unexpected, however, was the fact that 2-$PEG_{12,000}$ conjugates are able to unexpectedly increase AUC by over 10-fold. This dramatic increase in area under the curve was not proportional to the additional polymer weight. Clearly, therapeutic advantages are realized by this unexpected increase.

Example 11

Effect of pH on PEGylation

In order to probe this effect, the polymer conjugation (PEGylation) reaction of Examples 5–8 was repeated using $mPEG_{12,000}$ (no surfactant) at four different pHs, 5.4, 6.5, 8.0 and 10.0. The ratio of 2.6 grams of SC-$PEG_{12,000}$ to 1 gram of IFN (molar ratio 3.9:1) was used for the reactions at pH 5.4, 6.5 and 8.0 while the ratio of 2.1 grams of 25 SC-$PEG_{12,000}$ to 1 gram of IFN (molar ratio 3.2:1) was used at pH 10. At the end of the reaction, glycine was added to quench any residual PEGylation reagent. The product from each reaction was then purified using a Q-hyper D resin at pH 8 with salt elution to remove unreacted ingredients.

The purified conjugates obtained at the different pHs were evaluated for their biological activity, hydroxylamine sensitivity and distribution of positional isomers. Biological activity was determined by specific activity (MTT-CPE assay).

Hydroxylamine sensitivity was undertaken to determine what percentage of the conjugates were PEGylated at histidine sites, including the IFN-His34. Hydroxylamine is a known reagent that we have found to selectively cleave PEG from IFN histidines. An aliquot of each of the samples (50 µl) was diluted with 0.45 ml of 10 mM sodium phosphate pH 7.0. An aliquot of this protein solution (150 µl) was treated with 150 µl of 0.5 M hydroxylamine and incubated at room temperature for 60 minutes. Thereafter, a volume of 75 ill was loaded on a Mini-S column (Pharmacia Biotech) for cation exchange chromatography. Mobile phase A included 10 mM sodium acetate pH 5.3 buffer and 25% 2-propanol. Mobile phase B contained 500 mM sodium chloride dissolved in mobile phase A. The flow rate was set at 0.5 ml/min and the eluted protein was detected at 214nm. The individual PEG-IFN solutions were diluted with 10 mM sodium acetate pH 5.3, containing 2-propanol (5%) to 1 mg/ml protein concentration. Injection volumes ranged from 10 to 30 µl, depending upon the protein concentration. A linear gradient was used. The results are set forth in the Table 7 below and in FIG. 1.

FIG. 1 shows the overlay of the chromatograms obtained from the Mono-S cation exchange chromatography column of the different pH reaction products. The site of polymer conjugation for each positional isomer was determined by digestion of individual peaks from cation exchange chromatography using proteolytic enzymes (trypsin, V8-protease, chymotrypsin or subtilisin), isolation of PEGylated fragments, and analysis by N-terminal sequencing and mass spectroscopy.

As seen in the figure, the distribution of the positional isomers changes significantly as the pH of the reaction changes. The higher the pH, the less His34-linked PEG-IFN and, less dramatically, Cys1-linked PEG-IFN products are produced.

Table 7 summarizes the specific bioactivity as determined using the MTT-CPE bioassay for IFN and the amount of IFN released upon treatment with 0.5M hydroxylamine for 2 hours at 25° C. for the different conjugate products. These findings confirm that the differences seen in FIG. 1 can also be related to different biological characteristics of the products. When the conjugation is conducted at a higher pH (i.e. 8 or 10) the products formed are less bioactive and more resistant to hydroxylamine, which therefore means that at higher pH's, less polymer is on His34.

TABLE 7

Bioactivities and Hydroxylamine Sensitivities of PEG-IFNs Generated at Different pHs

| Reaction pH | Specific Activity (CPE assay) MIU/mg | % of Conjugate Converted to IFN by Hydroxylamine |
| --- | --- | --- |
| 5.4 | 61.8 | 56% |
| 6.5 | 74.5 | 47% |
| 8.0 | 33.3 | 8% |
| 10.0 | 27.8 | <1% |

The above results indicate that pH is a key variable of the conjugation reaction and that the relative distribution of the positional isomers varies dramatically with pH. Unexpectedly, the bioactivity of the resultant PEG-IFN mixture of positional isomers is also affected.

Example 12

Comparison of Urethane Linkage Forming Activated Polymers

In this example, effect of pH on reaction conditions was compared using a different type of urethane linker to see if the activating group had any role in determining the site of polymer attachment and bioactivity. In particular, the Methoxypoly(ethylene glycol)-succinimidyl carbonate MW 12,000 (SC-PEG$_{12,000}$) used in the earlier examples was compared with methoxypoly(ethylene glycol)-2-pyridyl carbonate, MW 12,000 (PC-PEG$_{12,000}$) disclosed in U.S. Pat. No. 5,382,657, as the activated polymer reagents for interferon alpha-2b (IFN). The conjugation reactions were carried out for both reagents, SC-PEG$_{12,000}$ and PC-PEG$_{12,000}$, at pH 6.5 and 10.0. The conditions used to generate the 4 monopegylated IFN samples for analysis were 1) SC-PEG$_{12,000}$ @ pH 6.5; 2) PC-PEG$_{12,000}$ @ pH 6.5; 3) SC-PEG$_{12,000}$ (1 pH 10.0; and 4) PC-PEG$_{12,000}$ @ pH 10.0. In each pH 6.5 case, a 3.9 to 1 molar ratio of PEG:IFN was used. In each pH 10.0 case, a 3.2:1 molar ratio of PEG:IFN was used. These conditions were chosen to evaluate the influence of both reaction pH and linker on the composition of the final product.

The conjugated material from each reaction condition was recovered and tested for biological activity (CPE assay) and for distribution of positional isomers using Mini-S chromatography assay.

The PEG-IFN generated by reacting IFN with PC-PEG$_{12,000}$ at pH 6.5 had lower biological activity than that made with SC-PEG$_{12,000}$ in spite of both reagents forming urethane bonds. Thus, it was shown that in spite of the similarity between the linkers, SC-PEG, an oxycarbonyl-oxy-N-dicarboximide-activated polymer, more preferentially attaches to His34. Interestingly, however, the PEG-IFN products generated by carrying out the reaction at pH 10 with both PC-PEG$_{12,000}$ and SC-PEG$_{12,000}$ had similar biological activities. In both cases, however, the activities were lower than that obtained for SC-PEG$_{12,000}$ at pH 6.5.

Mini-S chromatography assays showed that histidine-34-linked PEG-IFN is the major positional isomer present when using SC-PEG$_{12,000}$ at pH 6.5. Lysine-121-linked PEG-IFN is the major positional isomer present when the reaction is carried out at pH 6.5 using PC-PEG$_{12,000}$. At pH 10, Lysine-121-linked PEG-IFN is the major product using either reagent. See Table 8.

Thus, the use of acidic pH and an oxycarbonyl-oxy-N-dicarboximide-activated polymer, i.e. SC-PEG, produce conjugates which are unique products which cannot be reproduced by substituting another urethane bond-forming activated polymer such as PC-PEG$_{12,000}$ in place of SC-PEG$_{12,000}$.

The above materials contained less than 5% total di-PEG and multi-PEG-IFN as indicated by the size-exclusion HPLC assay.

TABLE 8

Summary of MiniS Assay Results

| Sample | PEAK NUMBER - (Area Percent) | | | | | | | |
|---|---|---|---|---|---|---|---|---|
| | 1 | 2 | 3 | 4 | 5 | 6 | 7 | 8 |
| SC-PEG; pH 6.5 | 2.1 | 63 | ND | 0.7 | 11.8 | 5.6 | 3.4 | 13.3 |
| PC-PEG; pH 6.5 | ND | 4.8 | 9 | 9.6 | 33.8 | 13 | 3.8 | 25.9 |
| SC-PEG; pH 10 | ND | ND | 14.8 | 11.2 | 57.6 | 9.5 | 3.1 | 3.8 |
| PC-PEG; pH 10 | ND | ND | 9.6 | 13.8 | 51.7 | 13.7 | 3.5 | 7.8 |

ND: not detected
Peak Assignment:
Peak 2: His-34 linked PEG-IFN ;
Peak 4: Lys-31 linked PEG-IFN;
Peak 5: Lys-121 linked PEG-IFN;
Peak 6: Lys-49 linked PEG-IFN;
Peak 7: Lys-83 Linked PEG-IFN;
Peak 8: N-terminus (cysteine) linked PEG-IFN

EXAMPLE 13

Cation Exchange Chromatography Characterization

In this example, analytical separation of several batches of PEG-IFN product produced using the procedure of Example 11 (pH 6.5) was carried out using cation exchange chromatography in order to determine the sites of polymer attachment and identify the individual positional isomers. The cation exchange apparatus was a Mini-S column (Pharmacia Biotech). Mobile phase A included 10 mM sodium acetate pH 5.3 buffer and 25% 2-propanol. Mobile phase B contained 500 mM sodium chloride dissolved in mobile phase A. The flow rate was set at 0.5 ml/min and the eluted protein was detected at 214 nm. The individual PEG-IFN solutions were diluted with 10 mM sodium acetate pH 5.3, containing 2-propanol (5%) to 1 mg/ml protein concentration. Injection volumes ranged from 10 to 30 µl, depending upon the protein concentration. The following linear gradient was used:

| Time (min) | A(%) | B(%) |
|---|---|---|
| 0 | 100 | 0 |
| 5 | 93 | 7 |
| 50 | 83 | 17 |
| 60 | 0 | 100 |
| 65 | 0 | 100 |
| 66 | 100 | 0 |
| 75 | 100 | 0 |

Figure 2:
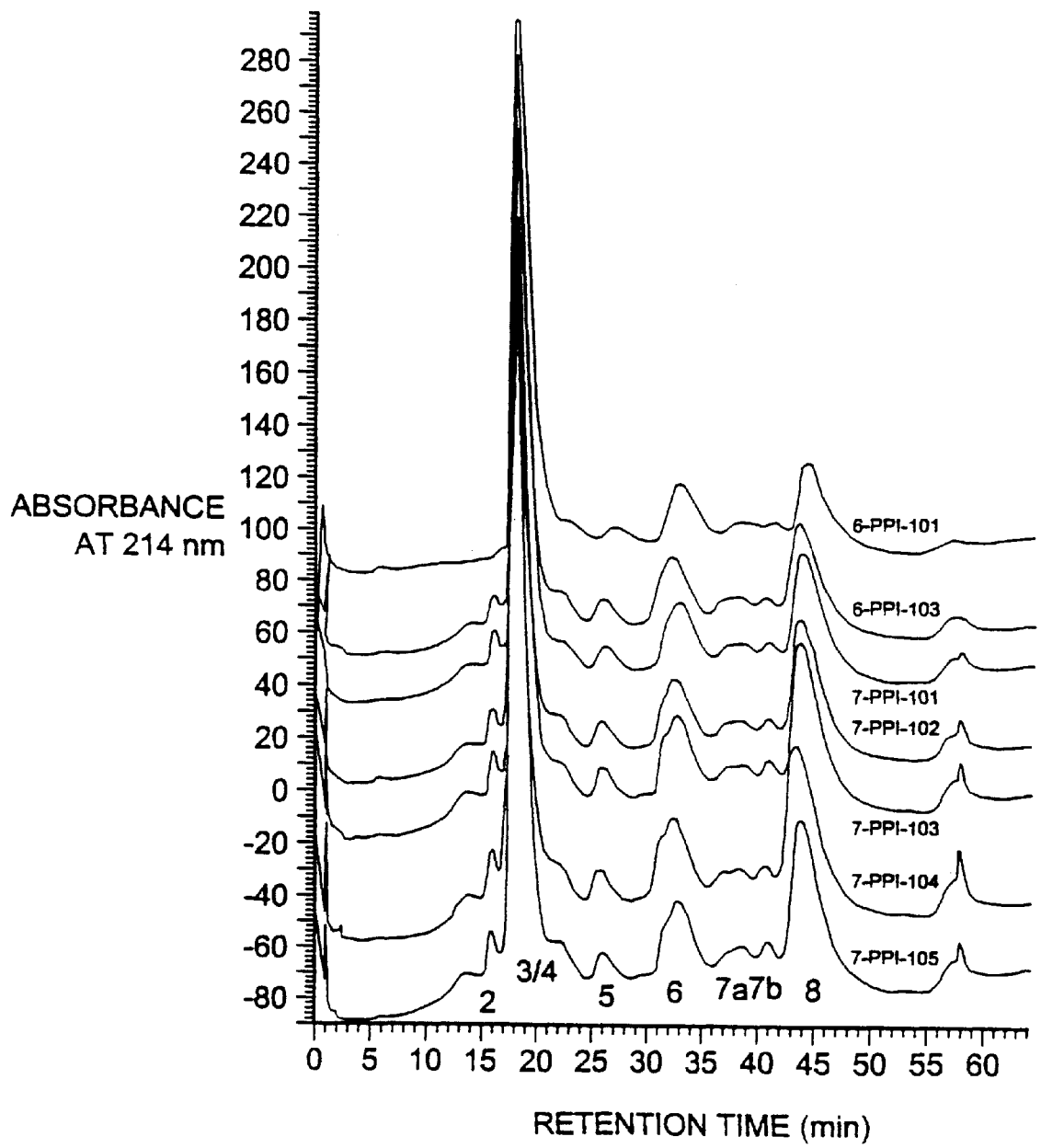
FIG. 2 is a series of chromatograms referred to in Example 13.

The results are provided in Table 9 below and graphically illustrated in FIG. 2.

TABLE 9

Area Percent Quantification of PEG-IFN Batches by Cation Exchange Chromotography

| Batch | Peak 2 | Peaks 3/4 | Peak 5 | Peak 6 | Peak 7a | Peak 7b | Peak 8 |
|---|---|---|---|---|---|---|---|
| 1 | 2.6 | 53.2 | 5.3 | 14.2 | 6.5 | 3.4 | 17.2 |
| 2 | 1.5 | 54.7 | 3.3 | 12.6 | 6.1 | 3.2 | 18.6 |
| 3 | 1.6 | 55.3 | 2.4 | 11.9 | 5.5 | 3.2 | 20.1 |
| 4 | 1.7 | 55.1 | 2.6 | 11.6 | 5.3 | 3.1 | 20.5 |
| 5 | 1.7 | 54.3 | 2.7 | 11.8 | 5.6 | 3.2 | 20.7 |

TABLE 9-continued

Area Percent Quantification of PEG-IFN Batches by Cation Exchange Chromotography

| Batch | Peak 2 | Peaks 3/4 | Peak 5 | Peak 6 | Peak 7a | Peak 7b | Peak 8 |
|---|---|---|---|---|---|---|---|
| 6 | 1.7 | 54.5 | 2.6 | 11.8 | 5.3 | 2.9 | 21.1 |
| 7 | 1.9 | 54.2 | 2.3 | 11.6 | 5.2 | 3.2 | 21.5 |

Main Peak Assignment: Peak 2: Lys-134 linked EPG-IFN; Peak 3/4: His-34 linked PEG-IFN; Peak 6: Lys-121 linked PEG-IFN and Lys-131 linked PEG-IFN; Peak 8: Cys-1 linked PEG-IFN.

These results illustrate that a majority of the conjugates were found in peaks 3 and 4 (His-34 linked PEG-IFN). The results also show that contrary to what was expected, most of the conjugates were formed by attaching the polymer to a histidine rather than one of the lysine amino groups.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

What is claimed is:

1. A pharmaceutical composition, comprising a mixture of alpha-interferon-conjugate positional isomers, wherein one of said positional isomers comprises an alpha-interferon covalently conjugated to a substantially non-antigenic alkyl terminated polyalkylene oxide at a histidine residue on said alpha interferon, so that said alpha interferon conjugates have a $T_{max}$ at least about 4 times greater than unmodified alpha-interferon measured under the same conditions.

2. The pharmaceutical composition of claim 1, wherein said alpha interferon conjugates have a $T_{max}$ at least about 8 times greater than unmodified alpha-interferon measured under the same conditions.

3. A pharmaceutical composition, comprising a mixture of alpha-interferon-conjugate positional isomers, wherein one of said positional isomers comprises an alpha-interferon covalently conjugated to a substantially non-antigenic alkyl terminated polyalkylene oxide at a histidine residue on said alpha interferon, so that said alpha interferon conjugates have an AUC at least about 10 times that of unmodified alpha-interferon measured under the same conditions.

4. The pharmaceutical composition of claim 1, wherein said polyalkylene oxide is polyethylene glycol.

5. The pharmaceutical composition of claim 1, wherein said alpha interferon conjugates have at least about 10% of the activity of unmodified alpha-interferon measured under the same conditions when said pharmaceutical composition is administered subcutaneously in a mammal.

6. The pharmaceutical composition of claim 3, wherein said alpha interferon conjugates have at least about 10% of the activity of unmodified alpha-interferon measured under the same conditions when said pharmaceutical composition is administered subcutaneously in a mammal.

7. The pharmaceutical composition of claim 1, wherein said alpha interferon conjugates have at least about 10% of the activity of unmodified alpha-interferon measured under the same conditions, and a $T_{1/2}$, of about 5 hours alpha phase when said conjugate is administered subcutaneously in a mammal.

8. The pharmaceutical composition of claim 3, wherein said alpha-interferon-conjugates have at least about 10% of the activity of unmodified alpha-interferon measured under the same conditions, and a $T_{1/2}$, of about 5 hours alpha phase when said pharmaceutical composition is administered subcutaneously in a mammal.

9. The pharmaceutical composition of claim 1, wherein said alpha interferon is interferon alpha 2b.

10. The pharmaceutical composition of claim 9, wherein said histidine residue is His34.

11. The pharmaceutical composition of claim 1, wherein said mixture of said alpha interferon conjugate positional isomers comprises at least about 3 positional isomers.

12. The pharmaceutical composition of claim 1 wherein said mixture of said alpha interferon positional isomers comprises at least about 6 positional isomers.

13. The pharmaceutical composition of claim 1, wherein said mixture of said alpha interferon conjugate positional isomers comprises at least about 8 positional isomers.

14. The pharmaceutical composition of claim 13, wherein said alpha interferon is alpha interferon 2b and said mixture of alpha interferon conjugate positional isomers comprises said polyalkylene oxide linked to said alpha interferon 2b, at an amino acid residue selected from the group consisting of Cys1, Lys31 His34, Lys49, Lys83, Lys121, Lys131, and Lys134.

15. The pharmaceutical composition of claim 4, wherein said polyalkylene oxide is a monomethoxy-polyethylene glycol, (mPEG).

16. The alpha-interferon-conjugate of claim 1 wherein said polyalkylene oxide is terminated with a $C_{1-4}$ alkyl.

17. The pharmaceutical composition of claim 1, wherein said polyalkylene oxide has a molecular weight of from about 200 to about 35,000.

18. A pharmaceutical composition, comprising a mixture of alpha interferon polymer conjugate positional isomers, wherein one of said positional isomers comprises an alpha interferon covalently conjugated to a substantially non-antigenic polymer at a histidine residue on said alpha interferon, wherein said substantially non-antigenic polymer is selected from the group consisting of polypropylene glycol, dextran, polyvinyl pyrrolidones, polyacryl amides, polyvinyl alcohols and carbohydrate-based polymers, so that said interferon conjugates have a $T_{max}$ at least about 4 times greater than unmodified alpha-interferon measured under the same conditions.

19. An alpha interferon-containing composition, comprising a plurality of alpha interferon polymer conjugates, wherein at least about 15% of the conjugates include covalent attachment of a substantially non-antigenic alkyl terminated polyalkylene oxide at a histidine of said alpha interferon, so that said interferon conjugates have a $T_{max}$ at least about 4 times greater than unmodified alpha-interferon measured under the same conditions.

20. The alpha interferon-containing composition of claim 19, wherein the alpha interferon portion of said alpha interferon-containing composition is alpha interferon 2b and said histidine is His34.

21. The alpha interferon-containing composition of claim 19, wherein at least about 30% of said conjugates include covalent attachment of said alkyl terminated polyalkylene oxide at histidine-34 of said alpha interferon.

22. A pharmaceutical composition comprising a mixture of alpha interferon 2b-polymer positional isomers, wherein from about 30 to about 60% of the positional isomers include a substantially non-antigenic alkyl terminated polyalkylene oxide conjugated to the His34 of said alpha interferon, from about 7 to about 20% of the positional isomers include a substantially non-antigenic alkyl terminated polyalkylene oxide conjugated to the Cys1 of said alpha interferon and about 7 to about 15% of the positional isomers include a substantially non-antigenic alkyl terminated polyalkylene oxide conjugated to the Lys121 of said alpha interferon, so that said interferon conjugates have a $T_{max}$ at least about 4 times greater than unmodified alpha-interferon measured under the same conditions.

* * * * *